US012036058B2

(12) United States Patent
Hiroshige et al.

(10) Patent No.: US 12,036,058 B2
(45) Date of Patent: Jul. 16, 2024

(54) IMAGING CONTROL DEVICE, IMAGE MANAGEMENT DEVICE, IMAGE MANAGEMENT SYSTEM, AND STORAGE MEDIUM

(71) Applicant: KONICA MINOLTA, INC., Tokyo (JP)

(72) Inventors: Akira Hiroshige, Kokubunji (JP); Ryo Watanabe, Toyohashi (JP); Sumiya Nagatsuka, Hino (JP); Ikki Nakamura, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 372 days.

(21) Appl. No.: 17/386,648

(22) Filed: Jul. 28, 2021

(65) Prior Publication Data

US 2022/0054100 A1 Feb. 24, 2022

(30) Foreign Application Priority Data

Aug. 19, 2020 (JP) .................. 2020-138401

(51) Int. Cl.
| | |
|---|---|
| *A61B 6/46* | (2024.01) |
| *A61B 6/00* | (2024.01) |
| *A61B 6/50* | (2024.01) |
| *G06T 7/00* | (2017.01) |
| *G16H 30/20* | (2018.01) |
| *G16H 40/40* | (2018.01) |
| *G16H 40/63* | (2018.01) |

(Continued)

(52) U.S. Cl.
CPC .............. *A61B 6/463* (2013.01); *A61B 6/465* (2013.01); *A61B 6/481* (2013.01); *G06T 7/0012* (2013.01)

(58) Field of Classification Search
None
See application file for complete search history.

(56) References Cited

U.S. PATENT DOCUMENTS

| | | | |
|---|---|---|---|
| 10,206,647 | B2 | 2/2019 | Hiroshige et al. |
| 10,898,148 | B2 | 1/2021 | Taneda |

(Continued)

FOREIGN PATENT DOCUMENTS

| | | | | |
|---|---|---|---|---|
| EP | 3119167 A1 | * | 1/2017 | ............. A61B 6/486 |
| EP | 2769675 B1 | * | 10/2017 | ............. A61B 6/463 |

(Continued)

OTHER PUBLICATIONS

Japanese Office Action (and English language translation thereof) dated Dec. 1, 2020 issued in Japanese Application No. 2020-138401.

*Primary Examiner* — Mohammed Rachedine
(74) *Attorney, Agent, or Firm* — Holtz, Holtz & Volek PC

(57) ABSTRACT

An imaging control device includes a hardware processor. The hardware processor generates second dynamic image data from first dynamic image data that is image data of a dynamic image having multiple frame images received from a radiographic image capturing device, the second dynamic image data being image data of a dynamic image having only a part of the multiple frame images; and transmits, to an external device, the second dynamic image data and information indicating a first radiation dose that is information corresponding to a radiation dose in imaging for obtaining the first dynamic image data.

20 Claims, 5 Drawing Sheets

(51) Int. Cl.
*H04N 5/14* (2006.01)
*H04N 5/91* (2006.01)

(56) References Cited

U.S. PATENT DOCUMENTS

| | | | |
|---|---|---|---|
| 10,966,674 B2 | 4/2021 | Nagatsuka | |
| 2013/0058453 A1* | 3/2013 | Kuwabara | A61B 6/542 378/97 |
| 2014/0079310 A1* | 3/2014 | Nakatsugawa | A61B 6/542 382/132 |
| 2014/0321606 A1* | 10/2014 | Funk | A61B 6/4064 378/205 |
| 2017/0238892 A1* | 8/2017 | Taneda | A61B 6/467 |
| 2018/0204326 A1* | 7/2018 | Noji | A61B 6/5217 |
| 2020/0074677 A1 | 3/2020 | Tezuka et al. | |
| 2021/0133967 A1 | 5/2021 | Matsutani et al. | |
| 2021/0186443 A1 | 6/2021 | Nagatsuka | |

FOREIGN PATENT DOCUMENTS

| | | | |
|---|---|---|---|
| JP | 2017144075 A | 8/2017 | |
| JP | 2018175320 A * | 11/2018 | |
| JP | 2020036694 A | 3/2020 | |
| JP | 6855223 B2 * | 4/2021 | G06K 9/3233 |
| WO | 2012164932 A1 | 12/2012 | |
| WO | WO-2020055951 A1 * | 3/2020 | A61K 51/0402 |

\* cited by examiner

IMAGING CONTROL DEVICE, IMAGE MANAGEMENT DEVICE, IMAGE MANAGEMENT SYSTEM, AND STORAGE MEDIUM

CROSS-REFERENCE TO RELATED APPLICATIONS

The entire disclosure of Japanese Patent Application No. 2020-138401 filed on Aug. 19, 2020 is incorporated herein by reference in its entirety.

BACKGROUND

Technological Field

The present invention relates to an imaging control device, an image management device, an image management system, and a storage medium.

Description of the Related Art

In X-ray plain imaging for obtaining a still image, dose management is conventionally performed in order to perform the imaging with a proper amount of radiation exposure. To be specific, each time imaging is performed, storing the image data which was obtained by the one imaging and the radiation dose in the one imaging so as to be associated with each other is conventionally performed.

Also in dynamic imaging for obtaining a dynamic image having multiple frame images, dose management is performed similarly to plain imaging. That is, storing the image data which was obtained by one imaging of dynamic imaging and the radiation dose in the one imaging so as to be associated with each other is performed.

In the plain imaging, as described in JP 2017-144075 A, for example, there is a technique of storing image data of a failed image and the radiation dose in the one imaging so as to be associated with each other and managing the image data and the radiation dose when the imaging failed and the failed image was generated.

SUMMARY

In diagnosis using the dynamic image, there is a request to delete or trim partial frame images (unnecessary frame images, frame images which are not the diagnosis target, and/or frame images to be thinned out in order to reduce the communication amount) among multiple frame images and to use only the remaining frame images.

For example, when multiple functions (for example, bloodstream function and ventilation functions and features of a part to be imaged (for example, lungs) are to be checked in single dynamic imaging, since the necessary frame images and frame images which are the diagnosis target vary, there is a request to take out different frame images corresponding to the functions and features to be checked from the same dynamic image.

In addition, the dynamic image is formed of many frame images, and the data amount is large. Thus, when the dynamic image is transmitted to the server or the like directly, the communication time increases and the server gets under a load. When all the frames are replayed, the replay time increases, which increases the load on the doctor who performs the diagnosis. Thus, there is also a request to reduce the data amount by thinning out the partial frame images from the dynamic image.

When the partial frame image is to be deleted or trimmed from the dynamic image obtained in the one imaging in this way, dose management is necessary.

The dose management in this case cannot be exactly the same as the dose management of a case of plain imaging for which deleting or trimming is performed by the unit of one imaging, and a case of performing dynamic imaging not deleting or trimming frame images.

However, consideration regarding the method of dose management in the dynamic imaging of generating image data formed of only the partial frame images is not progressed so much in the current situation.

The present invention has been made in consideration of the above matters, and an object of the present invention is to enable proper dose management even in a case of generating a dynamic image having partial frame images among all the frame images that were obtained by one imaging in the dynamic imaging.

To achieve at least one of the abovementioned objects, an imaging control device reflecting one aspect of the present invention is an imaging control device including a hardware processor that: generates second dynamic image data from first dynamic image data that is image data of a dynamic image having multiple frame images received from a radiographic image capturing device, the second dynamic image data being image data of a dynamic image having only a part of the multiple frame images; and transmits, to an external device, the second dynamic image data and information indicating a first radiation dose that is information corresponding to a radiation dose in imaging for obtaining the first dynamic image data.

To achieve at least one of the abovementioned objects, an image management device reflecting another aspect of the present invention is an image management device including a hardware processor that manages second dynamic image data and information indicating a first radiation dose, the second dynamic image data being image data of a dynamic image generated by deleting a partial frame image from first dynamic image data which is image data of a dynamic image having multiple frame images, and the information indicating the first radiation dose being information corresponding to a radiation dose in imaging for obtaining the first dynamic image data.

To achieve at least one of the abovementioned objects, an image management system reflecting another aspect of the present invention is an image management system including: a hardware processor that generates second dynamic image data from first dynamic image data that is image data of a dynamic image having multiple frame images received from a radiographic image capturing device, the second dynamic image data being image data of a dynamic image having only a part of the multiple frame images; and a storage that stores the second dynamic image data and information indicating a first radiation dose so as to be associated with each other, the information indicating the first radiation dose being information corresponding to a radiation dose in imaging for obtaining the first dynamic image data.

To achieve at least one of the abovementioned objects, a storage medium reflecting another aspect of the present invention is a non-transitory storage medium storing a computer readable program that causes a hardware processor of an imaging control device to perform: generating that is generating second dynamic image data from first dynamic image data which is image data of a dynamic image having multiple frame images received from a radiographic image capturing device, the second dynamic image data being image data of a dynamic image having only a part of the multiple frame images; and transmitting that is transmitting, to an external device, the second dynamic image data and information indicating a first radiation dose which is information corresponding to a radiation dose in imaging for obtaining the first dynamic image data.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

Hereinafter, one or more embodiments of the present invention will be described with reference to the drawings. However, the scope of the invention is not limited to the disclosed embodiments or the illustrated examples.
<1. Radiographic Imaging System>

First described is a schematic configuration of a radiographic imaging system (hereinafter referred to as a radiographic imaging system 100) according to this embodiment.

Figure 1:
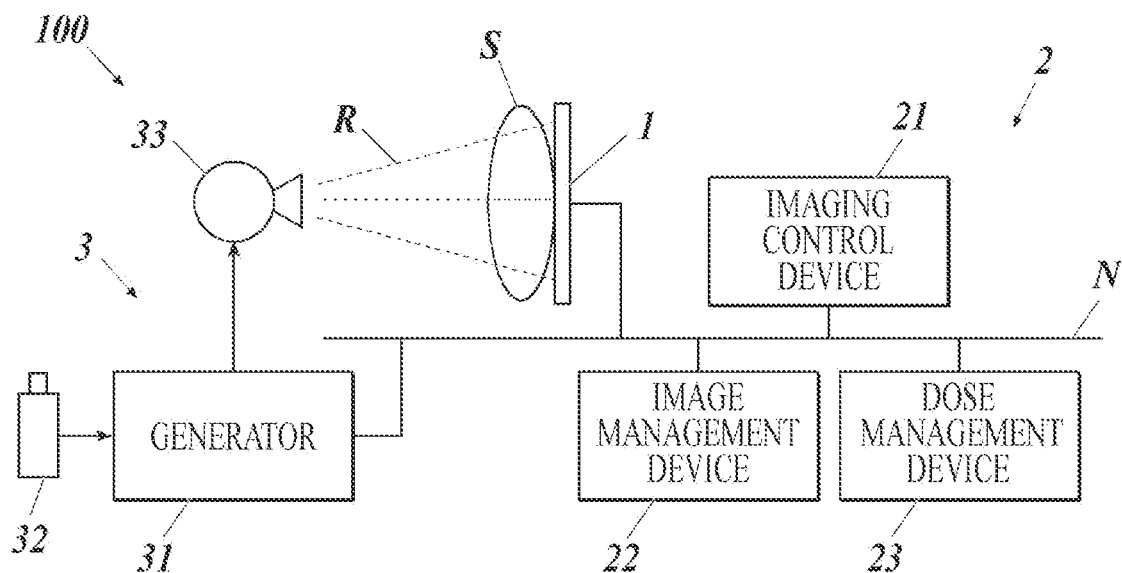
FIG. 1 is a block diagram showing a radiographic imaging system according to an embodiment of the present invention.

FIG. 1 is a block diagram of the radiographic imaging system 100.

The radiographic imaging system 100 includes a radiographic image capturing device (hereinafter, referred to as a radiographic image capturing device 1) and an image management system 2, as shown in FIG. 1.

The radiographic imaging system 100 according to this embodiment further incudes a radiation generating device (hereinafter, referred to as a radiation generating device 3).

The devices and system 1 to 3 can communicate with each other via a communication network N (local area network (LAN), wide area network (WAN), the Internet, or the like, for example.

The radiographic imaging system 100 may be installed in an imaging room, or may be configured to be movable (for example, a mobile medical vehicle).

The radiographic imaging system 100 may communicate with a hospital information system (HIS), a radiology information system (RIS), and the like.

[1-1. Radiation Generating Device]

The radiation generating device 3 includes a generator 31, an irradiation command switch 32, and a radiation source 33.

The generator 31 applies a voltage corresponding to preset imaging conditions to the radiation source 33 (tube) in response to operation of the irradiation command switch 32. The preset imaging conditions include, for example, a condition related to the subject S, such as a part to be imaged, an imaging direction, and a physique, or a condition related to radiation R irradiation such as a tube voltage, a tube current, an irradiation time, and a current time product (mAs value).

When a voltage is applied from the generator 31, the radiation source 33 generates radiation R (for example, X-rays) of a dose corresponding to the applied voltage.

The radiation generating device 3 generates radiation R in a manner according to a type of a radiographic image to be generated (a still image, a dynamic image composed of multiple frames).

For a still image, radiation R is emitted just one time in response to a single press of the irradiation command switch 32.

For a dynamic image, pulsed radiation R is repeatedly emitted multiple times per a predetermined time (for example, 15 times per second) in response to a single press of the irradiation command switch 32. Alternatively, radiation R is continuously emitted for a predetermined time.

The radiation generating device 3 according to the present embodiment outputs pulsed radiation dose information corresponding to the radiation dose of each pulsed radiation R each time the pulsed radiation R is generated.

[1-2. Radiographic Image Capturing Device]

The radiographic image capturing device 1 generates digital data of the radiographic image showing the part as an imaging target of the subject.

The radiographic image capturing device 1 according to the present embodiment is a portable FPD (Flat Panel Detector) device.

To be specific, though not shown in the drawings, the radiographic image capturing device 1 according to the present embodiment includes the followings: a sensor substrate in which imaging elements generating electric charges according to the dose by receiving the radiation R and switch elements accumulating and releasing the electric charges are arranged two-dimensionally (in a matrix shape); a scanning section that switches on/off of each of the switch elements; a readout section that reads out the amount of charge released from each of the pixels as a signal value; a control section that controls the sections and generates a radiographic image based on the signal values read by the readout circuit; a communication section that transmits the generated radiographic image data and various signals to external devices (such as the image management system 2 and the radiation generating device 3) and receives various kinds of information and various signals from the external devices; and the like.

The radiographic image capturing device 1 generates first dynamic image data that is image data of a dynamic image as well as still image data that is image data of a still image, by accumulating and releasing electric charges and reading the signal values in synchronization with the timing of emission of the radiation R from the radiation generating device 3.

In generating still image data, a radiographic image is generated just one time in response to a single press of the irradiation command switch 32.

In generating the first dynamic image data, a frame image that forms the dynamic image is repeatedly generated multiple times per a predetermined time (for example, 15 times per second) in response to a single press of the irradiation command switch 32.

The radiographic image capturing device may be a device integrated with the radiation generating device 3 (for example, CT (Computed Tomography) device, or the like).

The radiographic image capturing device 1 may display the generated dynamic image in real-time on a display connected to the radiographic image capturing device 1 (for example, in fluoroscopy).

[1-3. Image Management System]

The image management system 2 includes an imaging control device 21, an image management device 22, and a dose management device 23.

(Console)

The imaging control device 21 generates second dynamic image data (to be described later in detail) from the first dynamic image data received from the radiographic image capturing device 1.

The imaging control device 21 includes a personal computer (PC) and a dedicated device.

The imaging control device 21 according to the present embodiment also serves as a console.

That is, the imaging control device 21 according to the present embodiment has a function of setting various imaging conditions (a tube voltage, a tube current, an irradiation time (mAs value), a part to be imaged, an imaging direction, etc.) in at least one of the radiographic image capturing device 1 and the radiation generating device 3.

The imaging control device 21 according to the present embodiment sets the imaging conditions according to imaging order information obtained from other system(s) (HIS, RIS, etc) or operation by users (for example, technicians).

The imaging control device 21 may be separate from the console.

The imaging control device 21 may serve as device(s) other than the console, in addition to the console.

The details of the imaging control device 21 will be described later.

(Image Management Device)

The image management device 22 manages the second dynamic image data generated by the imaging control device 21.

The image management device 22 is a picture archiving and communication system (PACS), an image diagnosis workstation (IWS), or the like.

The image management device 22 may manage the image data (still image data, first dynamic image data, etc.) generated by the radiographic image capturing device as well as the second dynamic image data.

The image management device 22 may be separate from PACS and IWS.

The image management device 22 may serve as device(s) other than PACS and IWS, in addition to PACS or IWS.

The details of the image management device 22 will be described later.

(Dose Management Device)

The dose management device 23 manages first radiation dose information (to be described later in detail).

The image management device 22 includes a personal computer (PC), a dedicated device, a virtual server on a cloud, or the like.

The dose management device 23 may manage radiation dose information corresponding to the radiation dose for imaging other than the imaging for obtaining the first dynamic image data.

The dose management device 23 may be included in the image management device 22.

The details of the dose management device 23 will be described later.

[1-4. Schematic Operation of Radiographic Imaging System]

The radiographic imaging system 100 configured in this way operates as follows.

First, when the radiation generating device 3 emits radiation R to the part that is the imaging target of the subject S located between the radiographic image capturing device 1 and the radiation source 33 of the radiation generating device 3 arranged to face each other with a distance, the radiographic image capturing device 1 generates a radiographic image (still image, dynamic image) showing the part that is the imaging target, and transmits the image data (still image data, first dynamic image data) to the imaging control device 21.

In response to reception of the first dynamic image data, the imaging control device 21 generates the second dynamic image data from the first dynamic image data and transmits the second dynamic image data together with first radiation dose information to the image management system 2.

The image management system 2 manages the received second dynamic image data together with the first radiation dose information.

<2. Details of Imaging Control Device>

Next, the imaging control device 21 in the above-described radiographic imaging system 100 is described in detail.

Figure 2:
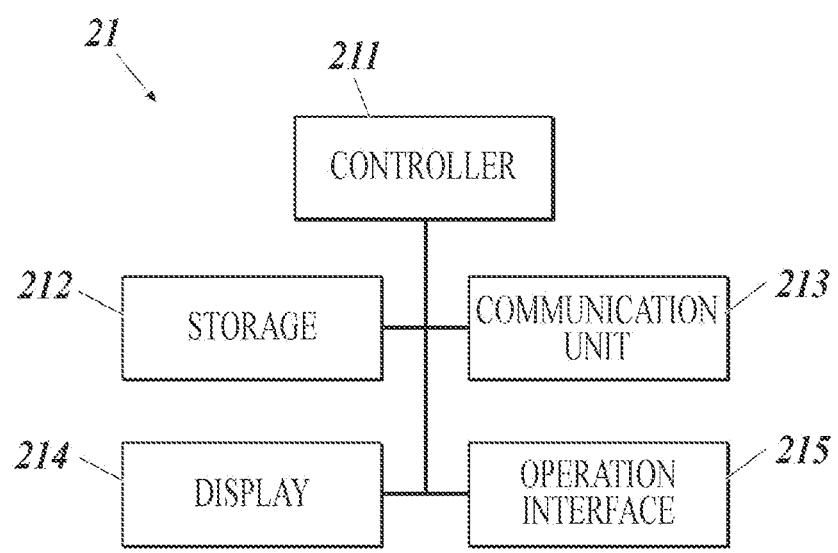
FIG. 2 is a block diagram showing an imaging control device included in the radiographic imaging system in FIG. 1.
Figure 3A:
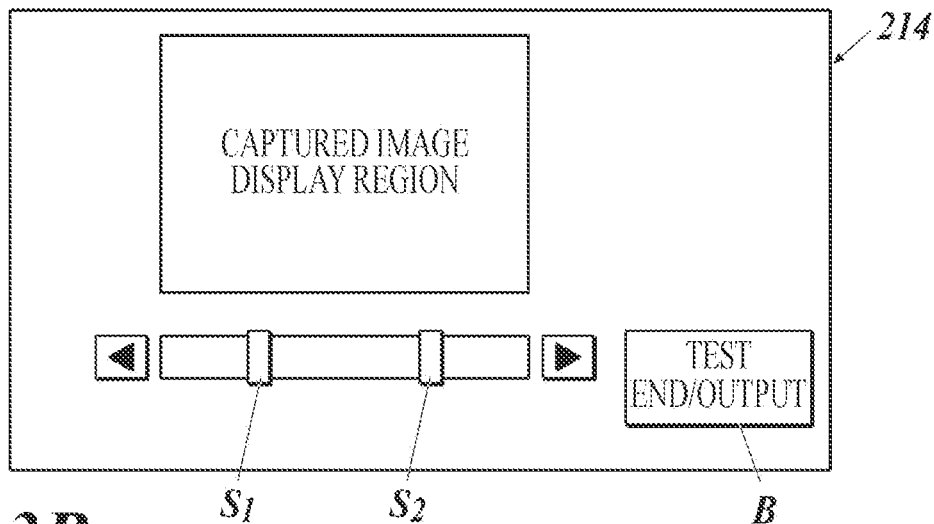
FIGS. 3A to 3C are views each showing an example of the method for selecting unnecessary frame images.
Figure 3B:
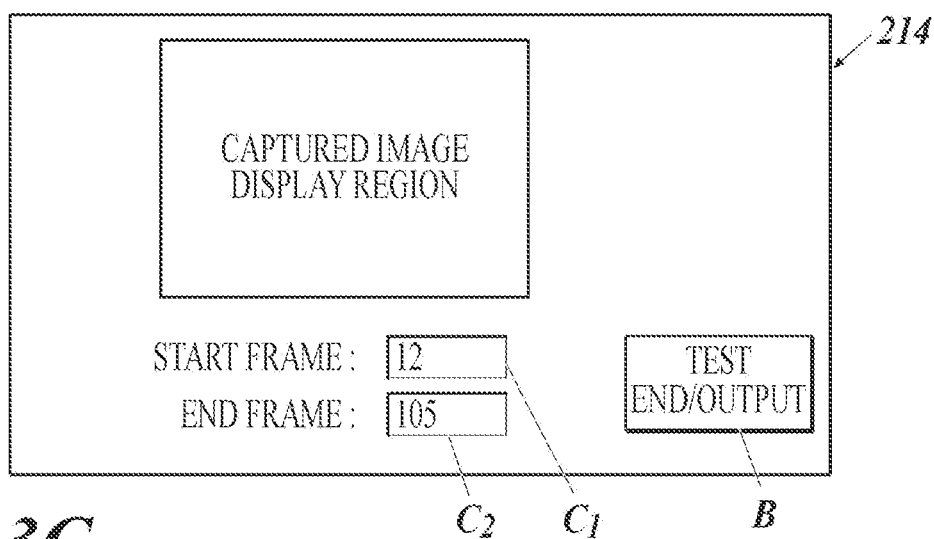
Figure 3C:
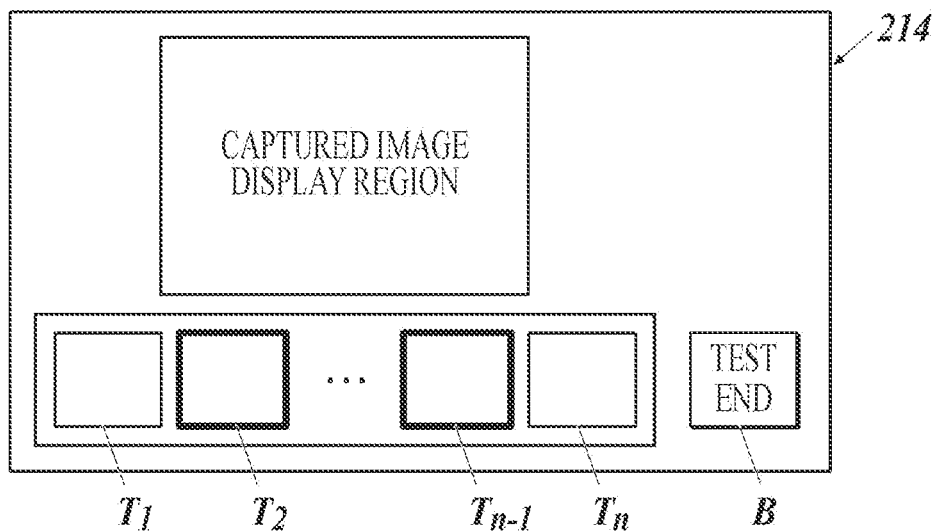
Figure 4A:
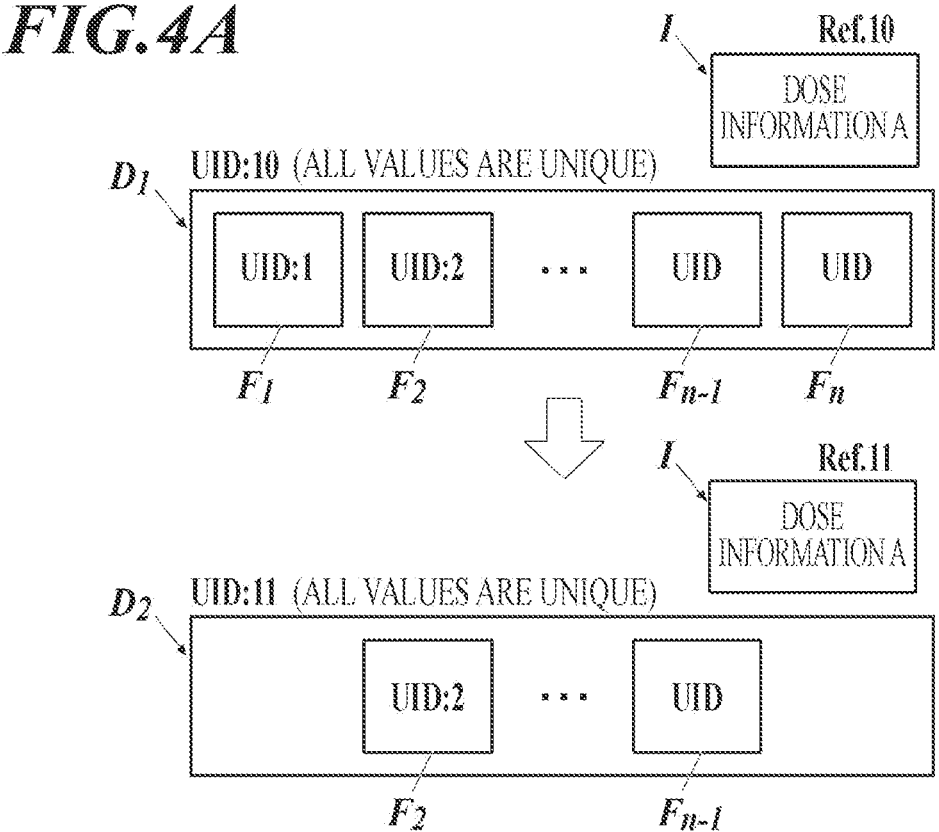
FIGS. 4A and 4B are views each showing an example of the method for associating second dynamic image data with first radiation dose information.
Figure 4B:
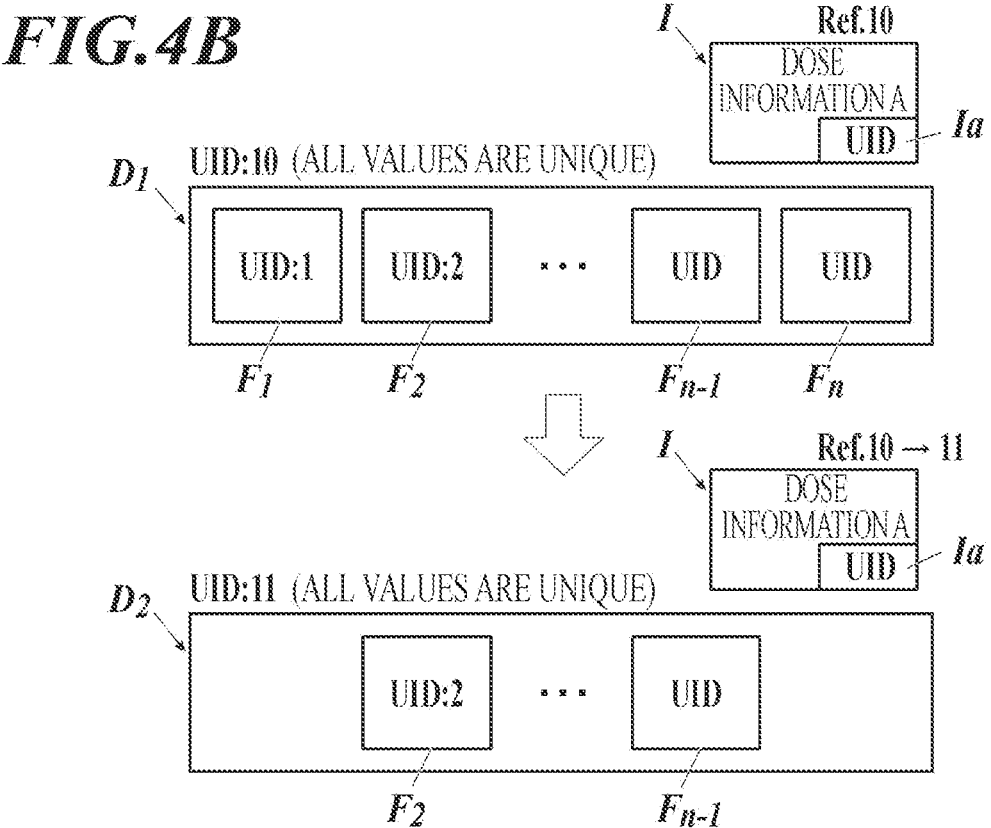

FIG. 2 is a block diagram showing the imaging control device 21. FIGS. 3A to 3C are views each showing an example of the method for selecting unnecessary frame images. FIGS. 4A and 4B are views each showing an example of the method for associating second dynamic image data with first radiation dose information.

[2-1. Configuration of Imaging Control Device]

The imaging control device 21 includes, as shown in FIG. 2, a controller 211 (hardware processor), a storage 212, a communication unit 213, a display 214, and an operation interface 215.

The components 211 to 215 are electrically connected with each other by a bus or the like.

The controller 211 includes a central processing unit (CPU), a random access memory (RAM), a read only memory (ROM), and the like.

The ROM stores various types of programs executed by the CPU, parameters necessary to execute the programs, and the like.

The CPU reads the various types of programs stored in the ROM, loads them in the RAM, executes various processes according to the loaded programs, and centrally controls the operation of each of the components of the imaging control device 21.

The storage 212 includes a non-volatile memory and a hard disk.

The storage 212 may store image data of radiographic images obtained from external device(s) (radiographic image capturing device 1, or the like).

The communication unit 213 includes a communication module.

The communication unit 213 transmits and receives various types of signals and data to and from external devices (radiographic image capturing device 1, image management device 22, dose management device 23, radiation generating device 3, etc.) connected by wire or wirelessly via a communication network N.

The display 214 includes, for example, a liquid crystal display (LCD), an electronic luminescent display (ELD), and a cathode ray tube (CRT).

The display 214 displays radiographic images according to image signals received from the controller 211.

The operation interface 215 includes a keyboard (cursor keys, number input keys, various function keys, etc.), a pointing device (a mouse, etc.), and a touch panel superimposed on the surface of the display 214.

The operation interface 215 outputs control signals according to operation by users to the controller 211.

The imaging control device 21 may not necessarily include the display 214 or the operation interface 215, and may receive control signals from an input device provided separately from the imaging control device 21 or output image signals to a display device (a monitor) provided separately from the imaging control device 21, via the communication unit 213, for example.

In the case where external device(s) (the image management device 22, dose management device 23, etc.) includes a display or an operation interface, the imaging control device 21 may receive control signals via an operation interface of the external device or output image signals to a display of the external device (a display and an operation interface may be shared with the external device).

[2-2. Operations of Imaging Control Device]

The controller 211 of the imaging control device 21 configured as described above performs the following various operations.

(Obtaining Process)

For example, the controller 211 executes the obtaining process in response to satisfaction of predetermined conditions as a trigger.

The predetermined conditions include, for example, turning on the power of the imaging control device 21, starting of the generation and transmission of frame images by the radiographic image capturing device 1, receiving a predetermined control signal from an external device, and a predetermined operation being made to the operation interface 215.

In this obtaining process, the controller 211 obtains the first radiation dose information.

This "first radiation dose information" is information corresponding to the radiation dose (first radiation dose) in the imaging for obtaining the first dynamic image data.

The first radiation dose information includes the first radiation dose and imaging conditions of the imaging for obtaining the first dynamic image data.

In the obtaining process according to the present embodiment, the controller 211 obtains the first radiation dose information by any of the following methods (1) to (3).

(1) receive from the generator 31 of the radiation generating device 3
(2) receive from a dosimeter not shown in the drawings
(3) calculate by the controller 211

In the case of using the method (1), for example, entire dose information in the radiation dose structured report (RDSR) form generated by the generator 31 is received as the first radiation dose information.

In the case of using the method (2), a dosimeter is provided between the radiographic image capturing device 1 and the radiation source 33, or on the surface or inside the radiographic image capturing device 1, and the dose delivered to the radiographic image capturing device 1 which was measured/calculated by the dosimeter at the time of imaging is received.

In the case of using the method (3), for example, the controller 211 calculates by the NDD method or on the basis of the pulse number.

In the case of using the NDD method, the controller 211 calculates the radiation dose on the basis of distance information from the radiographic image capturing device 1 to the subject, and the imaging conditions (a tube current, a tube voltage, etc.) received by the generator 31.

In the case of calculating on the basis of the pulse number, the controller 211 calculates the radiation dose on the basis of the number of times the pulsed radiation was emitted and the pulsed radiation dose information output each time the pulsed radiation is emitted by the radiation generating device 3.

After obtaining the first radiation dose information, the controller 211 associates, with the first radiation dose information, identification information for identifying that the information is the first radiation dose information.

The first radiation dose information may include the radiation dose for each of the multiple frame images of the first dynamic image data.

As for this first radiation dose information, in the obtaining process according to the present embodiment, the controller 211 calculates the radiation dose for each of the multiple frame images by calculating the S value per unit area of each frame image, for example.

The S value is the value corresponding to the density of the output image obtained as a result of normalization process when imaging is performed to the subject on arbitrary imaging conditions. The S value corresponds to the sensitivity of film necessary to finish the reference signal value set in ROI to the density specified by the density DL and DH.

The S value can be calculated by using various conventionally known techniques (for example, techniques described in JP 2018-149166 A, JP 2010-188041 A etc.).

In the obtaining process according to the present embodiment, the controller 211 may calculate the radiation dose on the basis of EI which is a dose index value of industry standard, instead of the S value.

(Generating Process)

The controller 211 executes the generating process in response to the satisfaction of predetermined conditions as a trigger.

The predetermined conditions include, for example, obtaining the dynamic image data from an external device, turning on the power of the imaging control device 21, receiving a predetermined control signal from an external devices, and a predetermined operation being made to the operation interface 215.

In this generating process, the controller 211 generates second dynamic image data from the first dynamic image data received from the radiographic image capturing device 1.

This "second dynamic image data" is dynamic image data which was generated by deleting partial frame image(s) from the first dynamic image data (which has only a part of the multiple frame images of the first dynamic image data).

In the generating process according to the present embodiment, the controller 211 generates the second dynamic image data by a different method according to the purpose.

For example, when the user intends to obtain a dynamic image not including failed frame images or obtain a dynamic image showing only the functions and features to be checked, the controller 211 generates the second dynamic image data by deleting or trimming (that includes deleting a partial region of the frame image) the unnecessary frame image(s) (failed frame image, or frame image not showing the functions or features to be checked).

The unnecessary frame image(s) is selected by any of the following methods (1) to (3), for example.
(1) select by displaying a seek bar as shown in FIG. 3A on the display 214, moving a slider $S_1$ among the two sliders $S_1$, $S_2$ of the seek bar to the position corresponding to the frame image which is the start point of deleting, and moving the other slider $S_2$ to the position corresponding to the frame image which is the end point of deleting
(2) select by displaying two numerical input columns $C_1$, $C_2$ as shown in FIG. 3B on the display 214, inputting the number of the frame image which is the start point of deleting in the numerical input column $C_1$, and inputting the number of frame image which is the end point of deleting in the other numerical input column $C_2$
(3) select by displaying thumbnails $T_1$ to $T_n$ of the respective frame images as shown in FIG. 3C on the display 214, and selecting the thumbnail corresponding to the unnecessary frame image When all the frame images are unnecessary frame images, in this generating process, the controller 211 deletes all the frame images included in the first dynamic image data.

On the other hand, when the purpose is to reduce the data amount of the dynamic image data, the controller 211 generates the second dynamic image data by thinning out frame images at predetermined intervals.

The frame images to be thinned out may be automatically selected according to a preset interval, or may be selected by the user using the methods as descried above.

In this way, since the unnecessary frame image(s) is omitted, the number of frame images of the second dynamic image data is smaller than that of the first dynamic image data. Thus, the second radiation dose corresponding to the second dynamic image data (total of radiation doses of pulsed radiation for obtaining the frame images included in the second dynamic image data) is smaller than that of the first radiation dose of the imaging for obtaining the first dynamic image data.

In the above generating process, the controller 211 may generate, from the first dynamic image data, third dynamic image data which is dynamic image data having only a part of the multiple frame images and is different from the second dynamic image data.

This "third dynamic image data" is dynamic image data having only the unnecessary (deleted or trimmed) frame image(s), for example.

In the generating process according to the present embodiment, as shown in FIG. 4A, for example, the controller 211 assigns frame identification information (for example, SOPInstanceUID (UID1, UID2, and so on)) for identifying the frame images $F_1$ to $F_n$ to the individual frame images $F_1$ to $F_n$ included in the first dynamic image data $D_1$.

The controller 211 also assigns first identification information for identifying that the data is the first dynamic image data $D_1$ (for example, SOPInstanceUID (UID10)) different from those assigned to the individual frame images $F_1$ to $F_n$) to the entire first dynamic image data $D_1$. The first identification information is associated with the first radiation dose information I in advance.

In the generating process according to the present embodiment, the controller 211 also assigns second identification information for identifying that the data is the second dynamic image data $D_2$ (for example, SOPInstanceUID (UID11)) different from those assigned to the individual frame images $F_1$ to $F_n$ and the first dynamic image data $D_1$) to the entire second dynamic image data $D_2$.

The controller 211 associates the second identification information (UID (11)) assigned to the entire second dynamic image data $D_2$ with the first radiation dose information I.

At this time, the controller 211 may refer to the first identification information (UID10) assigned to the first dynamic image data $D_1$ for the first radiation dose information I which is the target to be associated, or may associate the first radiation dose information I with the individual frame images $F_1$ to $F_n$ in advance and use the information associated with the frame images among the frame images $F_1$ to $F_n$ that were not omitted after generating the second dynamic image data $D_2$.

Thereby, the first and second dynamic image data $D_1$, $D_2$ are associated with the first radiation dose information I.

In the above generating process, the controller 211 may assign other identification information Ia (for example, Irradiation Event UID) to the first radiation dose information I.

Thereby, by referring to the other identification information Ia, even after the first dynamic image data $D_1$ and the second dynamic image data $D_2$ are transmitted to the image management device 22, it is possible to determine that the radiation dose information I associated with the first dynamic image data $D_1$ and the radiation dose information I associated with the second dynamic image data $D_2$ are the information obtained from a same imaging.

The controller 211 serves as a generator by executing the generating process which has been described above.

(Transmitting Process)

The controller 211 executes a transmitting process.

The controller 211 according to the present embodiment executes the transmitting process in response to that a predetermined operation button on the above display screen (for example, "test end/output" button B as shown in FIGS. 3A and 3B) was operated, as a trigger.

In the transmitting process, the controller 211 transmits the second dynamic image data and the first radiation dose information to the external device (image management device 22, dose management device 23, etc.) via the communication unit 213.

In the transmitting process according to the present embodiment, the controller 211 transmits the second dynamic image data to the image management device 22, and transmits the first radiation dose information to the dose management device 23.

As mentioned above, the identification information associated with the first radiation dose information is assigned to the first to third dynamic image data. Thus, in the transmitting process according to the present embodiment, transmitting each of the first radiation dose information and the second dynamic image data via the communication unit 213 by the controller 211 means transmitting, to the external device, the first radiation dose information and the second dynamic image data so as to be associated with each other.

When the predetermined operation button is operated, the controller 211 may not execute the transmitting process immediately, but may once store the second dynamic image data and the first radiation dose information in the storage 212 and thereafter transmit them to the image management device 22 and the dose management device 23.

The controller 211 may execute the process of once storing the second dynamic image data and the first radiation dose information in the storage 212 and thereafter transmitting them in response to that another operation button (for example, "trimming" button) different from the above predetermined operation button was operated, as a trigger.

In the case of generating the third dynamic image data in the above generating process and obtaining third radiation dose information in the above obtaining process, the controller 211 may associate the third dynamic image data with the third radiation dose information and transmit them to the external device, or the controller 211 may manage the third dynamic image data and the third radiation dose information. Thereby, it is possible to utilize the third dynamic image data and the third radiation dose information in education, conference and the like.

In addition, the data obtained by combining the frame images included in the second dynamic image data and the dynamic image data included in the third dynamic image data is the first dynamic image data, and the sum of the second radiation dose corresponding to the second dynamic image data and the third radiation dose corresponding to the third dynamic image data is the first radiation dose. Thus, by the above configuration, it is possible to manage the images and radiation doses by using the second dynamic image data and the third dynamic image data, without using the first dynamic image data.

When all the frame images were failed frame images (imaging failed) and reimaging was performed, in the transmitting process, the controller 211 does not transmit the dynamic image data for which all the frame images are failed frame images.

However, in the transmitting process, the controller 211 may transmit the first radiation dose in the dynamic imaging in which all the frame images were failed and the first radiation dose in the reimaging to the external device.

In this case, the controller 211 may transmit the total amount of the first radiation dose in the dynamic imaging in which all the frame images failed and the first radiation dose in the reimaging to the external device. Alternatively, the controller 211 may individually transmit the first radiation dose in the dynamic imaging in which all the frame images failed and the first radiation dose in the reimaging to the external device.

The controller 211 serves as a transmitter by executing the transmitting process described above.

(Others)

The controller 211 may calculate a failed image rate and manage the failed image rate.

The failed image rate is a rate of the number of failed frame images which were deleted to the total number of the frame images included in the first dynamic image data.

The controller 211 may transmit the calculated failed image rate to the external device (image management device 22, dose management device 23).

The controller 211 may not calculate the failed image rate but count the number of failed frame images, and transmit the counted number.

The external device (image management device 22 or dose management device 23) may include the function of managing the failed image rate or the number of failed frame images.

<3. Details of Image Management Device>

Next, the details of the image management device 22 included in the above radiographic imaging system 100 will be described.

Figure 5:
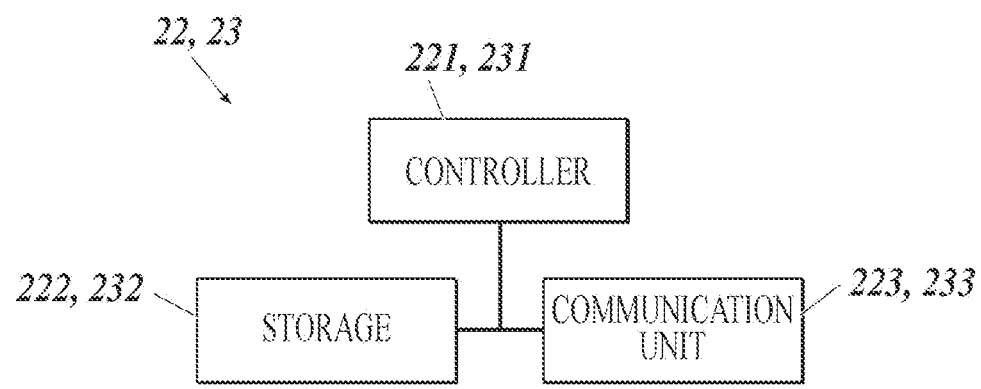
FIG. 5 is a block diagram showing an image management device (dose management devices included is the radiographic imaging system in FIG. 1.

FIG. 5 is a block diagram showing the image management device 22.

The second reference numeral in each pair of reference numerals in FIG. 5 is the reference numeral of the dose management device 23 described later.

[3-1. Configuration of Image Management Device]

The image management device 22 includes, as shown in FIG. 5, a controller 221 (hardware processor), a storage 222, and a communication unit 223.

The components 221 to 223 are electrically connected with each other by a bus or the like.

The image management device 22 may further include a display and an operation interface.

The controller 221 includes a CPU, a RAM, a ROM, and the like.

The ROM stores various types of programs executed by the CPU, parameters necessary to execute the programs, and the like.

The CPU reads the various types of programs stored in the ROM, loads them in the RAM, executes various processes according to the loaded programs, and centrally controls the operation of each of the components of the image management device 22.

The storage 222 includes a non-volatile memory and a hard disk.

The storage 222 stores the second dynamic image data received from the imaging control device 21.

The storage 222 may be configured to be able to store image data (for example, still image data, first and third dynamic image data, and the like) other than the second dynamic image data.

The communication unit 223 includes a communication module.

The communication unit 223 transmits and receives various types of signals and data to and from external devices (radiographic image capturing device 1, imaging control device 21, dose management device 23) connected by wire or wirelessly via a communication network N.

[3-2. Operations of Image Management Device]

The controller 221 of the image management device 22 configured as described above performs the following various operations.

For example, the controller 221 executes an image management process in response to satisfaction of predetermined conditions as a trigger.

The predetermined conditions include, for example, obtaining of the dynamic image data from the imaging control device 21, turning on the power of the image management device 22, and receiving a predetermined control signal from external device(s).

In the image management process, the controller 221 manages the second dynamic image data.

In the dose management process according to the present embodiment, the controller 221 manages the second dynamic image data by storing the second dynamic image data in the storage 222.

<4. Details of Dose Management Device>

Next, the details of the dose management device 23 included in the above radiographic imaging system 100 will be described.

[4-1. Configuration of Dose Management Device]

The dose management device 23 includes, as shown in FIG. 5, a controller 231 (hardware processor), a storage 232, and a communication unit 233.

The components 231 to 233 are electrically connected with each other by a bus or the like.

The dose management device 23 may further include a display and an operation interface.

The controller 231 includes a CPU, a RAM, a ROM, and the like.

The ROM stores various types of programs executed by the CPU, parameters necessary to execute the programs, and the like.

The CPU reads the various types of programs stored in the ROM, loads them in the RAM, executes various processes according to the loaded programs, and centrally controls the operation of each of the components of the dose management device 23.

The storage 232 includes a non-volatile memory and a hard disk.

The storage 232 stores the first radiation dose information received from the imaging control device 21.

The storage 232 may be configured to be able to store radiation dose information other than the first radiation dose information.

The communication unit 233 includes a communication module.

The communication unit 233 transmits and receives various types of signals and data to and from external devices (radiographic image capturing device 1, imaging control device 21, image management device 22) connected by wire or wirelessly via a communication network N.

[4-2. Operations of Dose Management Device]

The controller 231 of the dose management device 23 configured as described above performs the following various operations.

For example, the controller 231 executes a dose management process in response to satisfaction of predetermined conditions as a trigger.

The predetermined conditions include, for example, obtaining of the radiation dose information from the imaging control device 21, turning on the power of the dose management device 23, and receiving a predetermined control signal from external device(s).

In the dose management process, the controller 231 manages the first radiation dose information.

In the dose management process according to the present embodiment, the controller 221 manages the first radiation dose information by storing the first radiation dose information in the storage 232.

As mentioned above, the identification information (UID) associated with the first radiation dose information is assigned to the first to third dynamic image data. Thus, storing the first radiation dose information and the second dynamic image data in the storage 222 of the image management device 22 and in the storage 232 of the dose management device 23 respectively means storing the first radiation does information and the second dynamic image data so as to be associated with each other.

That is, in the image management system 2 according to the present embodiment, a set of the controller 221 of the image management device 22 and the controller 231 of the dose management device 23 serves as a manager, and a set of the storage 222 of the image management device 22 and the storage 232 of the dose management device 23 serves as a storage.

Even when all the frame images included in the first dynamic image data are the failed frame images and the imaging control device 21 does not transmit the second dynamic image data, the controller 231 may manage the corresponding first radiation dose information.

As mentioned above, the dose management device 23 may be included in the image management device 22.

In this case, the controller 221 of the image management device 22 associates the second dynamic image data and the first radiation dose information with each other and stores both of them in the storage 222.

That is, the controller 221 of the image management device 22 serves as a manager and the storage 222 serves as a storage.

<5. Specific Operation of Radiographic Imaging System>

Next, the specific operation of the above radiographic imaging system 100 will be described.

Figure 6:
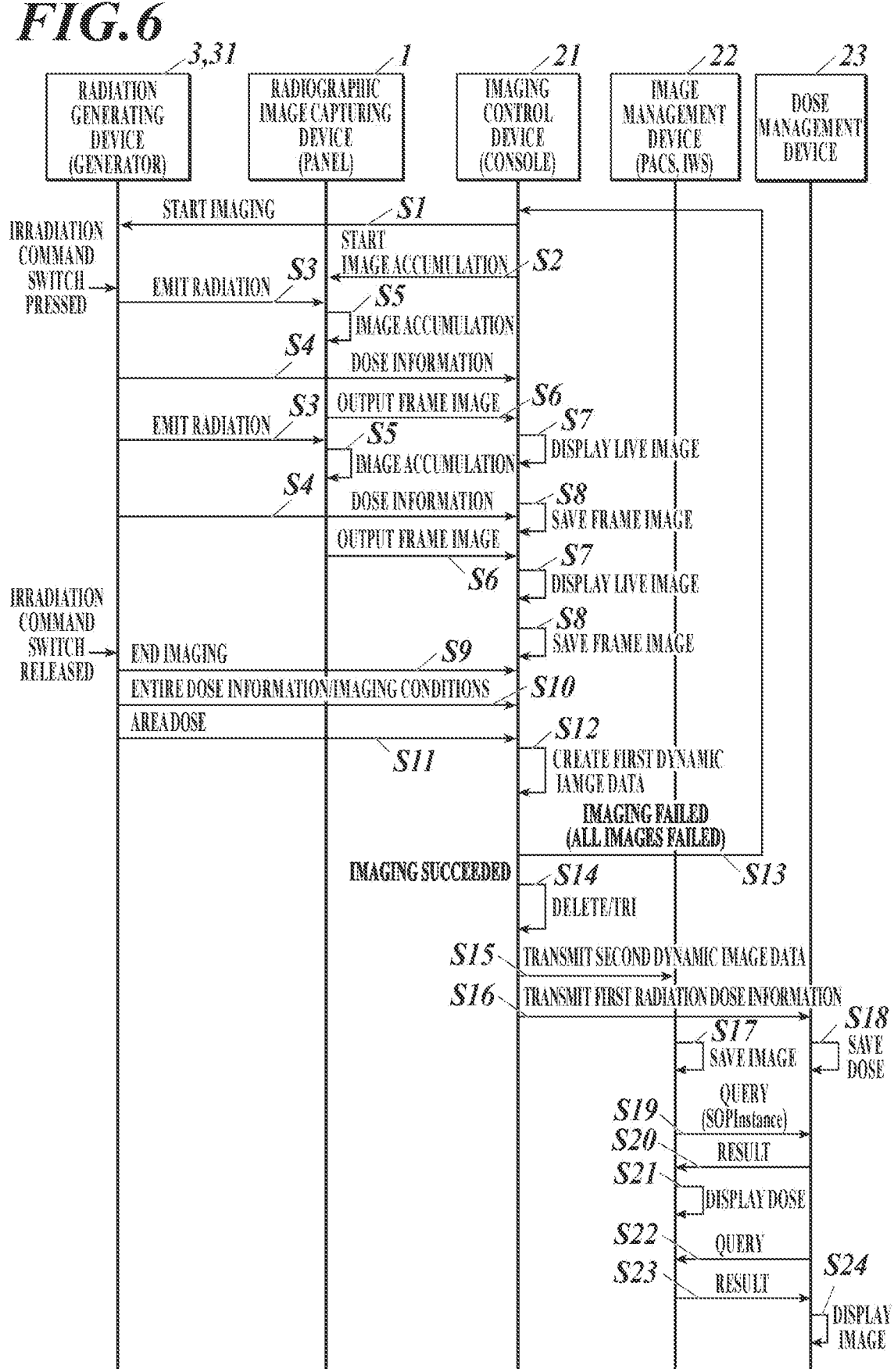
FIG. 6 is a sequence diagram showing an example of the flow of operation of the radiographic imaging system in FIG. 1.

FIG. 6 is a sequence diagram showing an example of the operation flow in the dynamic imaging of each of the devices forming the above radiographic imaging system 100.

The dynamic imaging using the radiographic imaging system 100 configured as described above is performed in the flow as shown in FIG. 6, for example.

First, the imaging control device 21 transmits the imaging start signal instructing to start imaging to the radiation generating device 3 (step S1), and transmits the accumulation start signal instructing to start accumulating and reading dark electric charges to the radiographic image capturing device 1 (step S2).

The radiation generating device 3 starts preparation for generating the radiation in response to reception of the imaging start signal.

The radiographic image capturing device 1 repeats the accumulation and reading of the dark electric charges in response to reception of the accumulation start signal.

When the irradiation command switch 32 is operated in a state in which the radiation generating device 3 performs preparation for generating radiation and the radiographic image capturing device 1 is repeating the accumulation of dark image, the radiation generating device 3 repeats generating pulsed radiation (step S3).

The radiation generating device 3 transmits the radiation dose information to the imaging control device 21 each time the pulsed radiation is generated (step S4).

The radiographic image capturing device 1 repeats generating a frame image (step S5) and transmitting the frame image (step S6) in synchronization with reception of the pulsed radiation R from the radiation generating device 3.

Each time the frame image data is received, the imaging control device 21 displays the frame image (step S7) and stores the frame image in the storage 212 (step S8).

When the irradiation command switch 32 is released, the radiation generating device 3 transmits an imaging end signal indicating that the imaging was finished to the imaging control device 21 (step S9), and transmits the entire dose information and/or imaging conditions to the imaging control device 21 as needed (step S10).

The radiation generating device 3 transmits the area dose to the imaging control device 21 as needed (step S11).

The imaging control device 21 generates the first dynamic image data after receiving all the frame images (step S12).

When all the frame images in the first dynamic image data are failed frame images (when all the frame images were selected as the unnecessary frame images), the imaging control device 21 returns to the operation of step S1 (perform imaging again; step S13).

On the other hand, when the partial frame image(s) in the first dynamic image data is failed frame image(s), the imaging control device 21 performs deleting or trimming of the unnecessary frame image(s) (executes the generating process: step S14), and generates the second dynamic image data. In the process, the imaging control device 21 performs image adjustment as needed.

After generating the second dynamic image data, the imaging control device 21 transmits the second dynamic image data to the image management device 22 (step S15), and transmits the first radiation dose information to the dose management device 23 (step S16).

In response to reception of the second dynamic image data, the image management device 22 saves the received second dynamic image data (stores the second dynamic image data in the storage 222) (step S17).

In response to reception of the first radiation dose information, the dose management device 23 saves the received first radiation dose information (stores the first radiation dose information in the storage 232) (step S18).

After saving the second dynamic image data, the image management device 22 transmits a query inquiring the first radiation dose information corresponding to the saved second dynamic image data (identification information (UID11) assigned to the second dynamic image data) to the dose management device 23 (step S19).

In response to reception of the query, the dose management device 23 transmits the result (the first radiation dose information associated with the identification information) to the image management device 22 (step S20).

In response to reception of the first radiation dose information, the image management device 22 displays the radiation dose corresponding to the first radiation dose information (step S21).

After saving the first radiation dose information, the dose management device 23 transmits a query requiring the second dynamic image data corresponding to the saved first radiation dose information (identification information (UID10) assigned to the first radiation dose information) to the image management device 22 (step S22).

In response to reception of the query, the dose management device 23 transmits the result (the second dynamic image data to which the identification information is assigned) to the dose management device 23 (step S23).

In response to reception of the second dynamic image data, the dose management device 23 displays the dynamic image based on the second dynamic image data (step S24).

Only one of the operation of steps S19 to S21 and the operation of steps S22 to S24 may be performed.

<6. Effects>

The imaging control device 21 which has been described above generates second dynamic image data having only a part of multiple frame images from first dynamic image data having the multiple frame images which have been received from a radiographic image capturing device 1. The imaging control device 21 transmits the second dynamic image data and first radiation dose information corresponding to the radiation dose in the imaging for obtaining the first dynamic image data to an external device(s).

The image management device 22 and the dose management device 23 manage the second dynamic image data and the first radiation dose information corresponding to the radiation dose in the imaging for obtaining the first dynamic image data.

Thus, by the imaging control device 21, the image management device 22 and the dose management device 23, it is possible to appropriately perform the dose management even in the case of generating a dynamic image which has partial frame image(s) among all the frame images which were obtained by one imaging in the dynamic imaging.

<7. Others>

The present invention is not limited to the above embodiment or the like, and modifications can be made as needed within the scope of the present invention.

For example, the above description discloses an example of using a hard disk, semiconductor nonvolatile memory, or the like as a computer readable medium of a program according to the present invention. However, the medium is not limited to this example. As other computer readable medium, a portable storage medium such as a CD-ROM can be applied. A carrier wave can also be applied as a medium providing the program data according to the present invention via a communication line.

Although embodiments of the present invention have been described and illustrated in detail, the disclosed embodiments are made for purposes of illustration and example only and not limitation. The scope of the present invention should be interpreted by terms of the appended claims.

What is claimed is:

1. An imaging control device comprising a hardware processor that:
receives first dynamic image data that is image data of a dynamic image including multiple frame images obtained by a radiographic image capturing device;
generates second dynamic image data from the received first dynamic image data, the second dynamic image data being image data of a dynamic image and including a plurality of the multiple frame images included in the first dynamic image data; and
transmits, to an external device, (i) the second dynamic image data and (ii) first radiation dose information, the first radiation dose information indicating a first radiation dose corresponding to a radiation dose used in an imaging process in which the first dynamic image data was obtained,
wherein at least one of the multiple frame images included in the first dynamic image data is not included in the second dynamic image data.

2. The imaging control device according to claim 1, wherein a second radiation dose corresponding to the second dynamic image data is smaller than the first radiation dose.

3. The imaging control device according to claim 1, wherein the hardware processor associates the first radiation dose information with the second dynamic image data and transmits the first radiation dose information and the second dynamic image data to the external device.

4. The imaging control device according to claim 1, wherein the first radiation dose information includes at least one of a radiation dose received from a generator that applies a voltage to a radiation source, an imaging condition, and a radiation dose received from a dosimeter.

5. The imaging control device according to claim 1, wherein the first radiation dose information is calculated based on distance information from the radiographic image capturing device to a subject and an imaging condition received from a generator that applies a voltage to a radiation source.

6. The imaging control device according to claim 1, wherein the hardware processor generates the second dynamic image data by deleting a failed frame image.

7. The imaging control device according to claim 6, wherein a failed image rate is calculated, the failed image rate being a rate of a number of deleted failed frame images to a total number of the multiple frame images included in the first dynamic image data.

8. The imaging control device according to claim 1, wherein the hardware processor generates the second dynamic image data by thinning out the multiple frame images included in the first dynamic image data at a predetermined interval.

9. The imaging control device according to claim 1, wherein the first radiation dose information includes a radiation dose for each of the multiple frame images included in the first dynamic image data.

10. The imaging control device according to claim 9, wherein the radiation dose for each of the multiple frame images is calculated by calculating an S value per unit area of each of the multiple frame images.

11. The imaging control device according to claim 9, wherein a radiation dose of a frame image excluded from the multiple frame images included in the first dynamic image data is managed.

12. The imaging control device according to claim 11, wherein a failed image rate is managed, the failed image rate being a rate of a number of deleted failed frame images to a total number of the multiple frame images included in the first dynamic image data.

13. The imaging control device according to claim 1, wherein the hardware processor generates third dynamic image data different from the second dynamic image data from the first dynamic image data, the third dynamic image data being image data of a dynamic image and including a plurality of the multiple frame images included in the first dynamic image data that are not included in the second dynamic image data.

14. The imaging control device according to claim 1, wherein, regarding dynamic imaging for which all frame images fail and reimaging is performed, (i) a total amount of information indicating a first radiation dose in the dynamic imaging for which all the frame images fail and information indicating a first radiation dose in the reimaging is transmitted to the external device, or (ii) the information indicating the first radiation dose in the dynamic imaging for which all the frame images fail and the information indicating the first radiation dose in the reimaging are individually transmitted to the external device.

15. An image management device comprising a hardware processor that manages second dynamic image data and information indicating a first radiation dose, the second dynamic image data being image data of a dynamic image generated by deleting at least one frame image from among multiple frame images included in first dynamic image data which is image data of a dynamic image, and the information indicating the first radiation dose being information corresponding to a radiation dose used in an imaging process in which the first dynamic image data was obtained.

16. The image management device according to claim 15, further comprising a storage that stores the second dynamic image data and the information indicating the first radiation dose.

17. The image management device according to claim 16, wherein the storage stores the information indicating the first radiation dose and the second dynamic image data so as to be associated with each other.

18. An image management system comprising:
a hardware processor that:
receives first dynamic image data that is image data of a dynamic image including multiple frame images obtained by a radiographic image capturing device; and
generates second dynamic image data from the received first dynamic image data, the second dynamic image data being image data of a dynamic image and including a plurality of the multiple frame images included in the first dynamic image data; and
a storage that stores, in association with each other, (i) the second dynamic image data and (ii) first radiation dose information, the first radiation dose information indicating a first radiation dose corresponding to a radiation dose used in an imaging process in which the first dynamic image data was obtained, and
wherein at least one of the multiple frame images included in the first dynamic image data is not included in the second dynamic image data.

19. The image management system according to claim 18, wherein the hardware processor transmits the second dynamic image data and the first radiation dose information.

20. A non-transitory computer readable storage medium storing a program that is executable by a hardware processor of an imaging control device to control the hardware processor to perform processes comprising:
receiving first dynamic image data which is image data of a dynamic image including multiple frame images obtained by a radiographic image capturing device;
generating second dynamic image data from the received first dynamic image data, the second dynamic image data being image data of a dynamic image and including a plurality of the multiple frame images included in the first dynamic image data; and
transmitting, to an external device, (i) the second dynamic image data and (ii) first radiation dose information, the first radiation dose information indicating a first radiation dose corresponding to a radiation dose used in an imaging process in which the first dynamic image data was obtained,
wherein at least one of the multiple frame images included in the first dynamic image data is not included in the second dynamic image data.

* * * * *